US011173189B2

(12) United States Patent
Wegiel et al.

(10) Patent No.: US 11,173,189 B2
(45) Date of Patent: Nov. 16, 2021

(54) DAPTOMYCIN FORMULATIONS CONTAINING A COMBINATION OF SORBITOL AND MANNITOL

(71) Applicants: BAXTER INTERNATIONAL INC., Deerfield, IL (US); BAXTER HEALTHCARE SA, Glattpark (CH)

(72) Inventors: Lindsay Wegiel, Martinsville, IN (US); Reagan Miller, Grayslake, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 17/199,086

(22) Filed: Mar. 11, 2021

(65) Prior Publication Data

US 2021/0283214 A1    Sep. 16, 2021

Related U.S. Application Data

(60) Provisional application No. 62/988,734, filed on Mar. 12, 2020, provisional application No. 63/083,434, filed on Sep. 25, 2020.

(51) Int. Cl.
| | | |
|---|---|---|
| *A61K 38/12* | (2006.01) | |
| *A61K 47/26* | (2006.01) | |
| *A61K 9/00* | (2006.01) | |
| *A61K 47/02* | (2006.01) | |
| *A61K 9/08* | (2006.01) | |

(52) U.S. Cl.
CPC ............ *A61K 38/12* (2013.01); *A61K 9/0019* (2013.01); *A61K 9/08* (2013.01); *A61K 47/02* (2013.01); *A61K 47/26* (2013.01)

(58) Field of Classification Search
CPC .. A61K 2039/505; A61K 38/12; A61K 47/26; A61K 47/02; A61K 9/0019; A61K 9/08; C07K 16/00; C07K 16/065; C07K 16/2809; C07K 16/461; C07K 16/468; C07K 2317/14; C07K 2317/24; C07K 2317/31; C07K 2317/526; C07K 2317/55; C07K 2317/569
See application file for complete search history.

(56) References Cited

U.S. PATENT DOCUMENTS

| | | | |
|---|---|---|---|
| 5,952,300 | A | 9/1999 | Nerurkar et al. |
| 7,115,663 | B2 | 10/2006 | Moye-Sherman et al. |
| 7,495,030 | B2 | 2/2009 | Gschneidner |
| 8,003,673 | B2 | 8/2011 | Alder et al. |
| 8,431,539 | B2 | 4/2013 | Palepu et al. |
| 8,835,382 | B2 | 9/2014 | O'Connor et al. |
| 9,138,456 | B2 | 9/2015 | O'Connor et al. |
| 9,655,946 | B2 | 5/2017 | Alexiou et al. |
| 9,662,397 | B2 | 5/2017 | O'Connor et al. |
| 10,933,019 | B2 | 3/2021 | Gjoni et al. |
| 2004/0067878 | A1 | 4/2004 | Hill et al. |
| 2005/0027113 | A1 | 2/2005 | Miao et al. |
| 2005/0152979 | A1 | 7/2005 | Besman et al. |
| 2006/0029599 | A1 | 2/2006 | Kaisheva et al. |
| 2009/0053149 | A1 | 2/2009 | Corcoran et al. |
| 2013/0172271 | A1 | 7/2013 | Fragale |
| 2015/0216928 | A1 | 8/2015 | Chetlapalli et al. |
| 2017/0216396 | A1 | 8/2017 | Alexiou et al. |
| 2017/0239335 | A1 | 8/2017 | Sonavaria et al. |
| 2017/0348382 | A1 | 12/2017 | Kurade et al. |
| 2018/0177843 | A1 | 6/2018 | Alexiou et al. |

FOREIGN PATENT DOCUMENTS

| | | | |
|---|---|---|---|
| CN | 1616083 | | 5/2005 |
| EP | 0386 951 | | 9/1990 |
| EP | 0386951 | | 9/1990 |
| EP | 0386951 | A2 | 9/1990 |
| EP | 2119449 | | 11/2009 |
| EP | 2 504 353 | | 10/2012 |
| EP | 3 417 849 | | 12/2018 |
| IN | 201841024220 | * | 6/2018 |
| WO | 9310809 | | 6/1993 |
| WO | 9745135 | | 12/1997 |

(Continued)

OTHER PUBLICATIONS

IN201841024220 Foreign patent finder, full text specification. 7 pages. Published Jan. 3, 2020. (Year: 2020).*
IN201841024220 Foreign patent finder, abstract. 2 pages. Published Jan. 3, 2020. (Year: 2020).*
Franks, "Freeze-drying of bioproducts: putting priniciples into practice," European Journal of Pharmaceutics and Biopharmaceutics 45 (1998), pp. 221-229.
Nail, "Fundamentals of Freeze-Drying," Pharmaceutical biotechnology, Development and Manufacture of Protein Pharmaceuticals, Feb. 2002—82 pages.
Wang, "Lyophilization and development of solid protein pharmaceuticals," International Journal of Pharmaceutics 203 (2000), pp. 1-60.

(Continued)

*Primary Examiner* — Marcela M Cordero Garcia
(74) *Attorney, Agent, or Firm* — K&L Gates LLP

(57) ABSTRACT

In an aspect, a method of manufacture of a pharmaceutically acceptable solid composition containing daptomycin includes drying an aqueous solution containing (i) water, (ii) the daptomycin, (iii) sorbitol in an amount of about 1.2 wt. % to about 9.0 wt. % of total volume of the aqueous composition and (iv) mannitol in an amount of about 0.6 wt. % to about 9.5 wt. % of total volume of the aqueous composition to form the solid composition. The drying can include an sublimation drying of about −25° C. to about 50° C. for a time period of about 15 hours to about 120 hours, most preferably about 15° C. for about 20 hours, optionally preceded and/or followed by one or more additional drying steps. Other aspects are the solid composition containing the daptomycin and also methods of treating a bacterial infection including administering a pharmaceutically acceptable product made by reconstituting the solid composition.

30 Claims, 21 Drawing Sheets

(56) References Cited

FOREIGN PATENT DOCUMENTS

| WO | 0153330 | 7/2001 |
| WO | 2007061529 | 5/2007 |
| WO | 2008012310 | 1/2008 |
| WO | 08150479 | 12/2008 |
| WO | 2009002481 | 12/2008 |
| WO | 2011062676 | 5/2011 |
| WO | 2011063419 | 5/2011 |
| WO | 2016 059592 | 4/2016 |
| WO | 2016098009 | 6/2016 |
| WO | 2018073269 | 4/2018 |
| WO | WO 2020128507 A1 | 6/2020 |
| WO | WO 2020229369 A1 | 11/2020 |

OTHER PUBLICATIONS

Wikipedia, "pH" https://en.wikipedia.org/wiki/PH, Oct. 4, 2019—11 pages.

Wikipedia, https://en.wikipedia.org/w/index.php?title=PH&oldid=326684718—9 pages.

Carpenter et al., "Rational Design of Stable Lyophilized Protein Formulations: Some Practical Advice," Pharmaceutical Research, vol. 14, No. 8 (1997)—7 pages.

European patent EP 2 504 353 B1, Application No. 10832379.1 Patentee: Cubist Pharmaceuticals LLC (CH), Opponent: Pajaro Ltd., Facts and Arguments (Rule 76(2)(c) EPC)—51 pages.

Cubicin (daptomycin for injection) Rx only—28 pages.

Muangsir et al., "The Kinetics of the Alkaline Degradation of Daptomycin," Division of Pharmaceutics, College of Pharmaceutics, College of Pharmacy, The University of Iowa City, Iowa—10 pages.

Carpenter et al., "Rational Design of Stable Lyophilized Protein Formulations: Theory And Practice," Center for Pharmaceutical biotechnology, University of Colorado—25 pages.

Naish et al. (2009) "Medical Sciences—Student Consult," First Published 2009 Main edition ISBN: 978 0 702 026 799, International edition ISBN 978 0 702 026 805—full text searchable online—5 pages.

Lewis et al. (1959) J.Am. Chem. Soc., "Purification and Chracterization of the Antiviral Agent Helenine," and Onthe Effect of Dose Rate on the Radiolysis of Liquid Hydrocarbons, Communications to the Editor dated Aug. 5, 1990—p. 4115.

Dobson et al., (2001), "Foundations of Chemical Biology," Oxford University Press—3 pages.

Yoshioka et al., "Stability of Drugs and Dosage Forms," Kluwer Academic Publishers—6 pages.

Remingtons Pharmaceutical Sciences, 17th Edition 1985, Mack Publishing Company pp. 1538 to 1539, Chapter 85—4 pages.

Allen et al., "Ansel's Pharma eutical Dosage Forms and Drug Delivery Systems," Ninth Edition 2005—57 Pages.

Katdare and Chaubal, "Excipient Development for Pharmaceutical, Biotechnology, and Drug Delivery Systems," Informa healthcare, 2006—50 pages.

Ward et al., "Protection of the enzyme L-asparaginase during lyophilisation—a molecular modelling approach to predict required level of lyoprotectant," International Journal of Pharmaceutics, vol. 187 (1999), pp. 153-162.

Carpenter et al., "Rational Design of Stable Lyophilized Protein Formulations: Some Practical Advice," Pharmaceutical Research, vol. 14, No. 8, 1997, pp. 969-975.

Pharmaceutical Technology Editors, "Variables Affecting Reconstitution Time of Dry Powder for Injection," Pharmaceutical Technology, vol. 32, Issue 7—16 pages.

Eisenstein et al., "Daptomycin: From the Mountain to the Clinic, with Essential Help from Francis Tally, MD," CID 2010:50 (Suppl 1)—S10-S14.

Frankenfeld et al., "Daptomycin: a comparison of two intravenous formulations," Drug, Design, Development and Therapy, 2018, vol. 12, pp. 1953-1958.

Scientific Discussion, EMEA 2006—40 pages.

Cubicin article (daptomycin for injection), Cubist Pharmaceuticals, Inc., US Drug label for Cubicin, Mar. 2007—28 pages.

Cubicin RF article, (daptomycin for injection), Highlights of Prescribing Information, Mar. 2017—36 pages.

Guidance on INN, Guidelines on the Use of INNs for Pharmaceutical Substances (1997), World Health Organization, https://www.who.int/medicines/services/inn/innquidance/en/—3 pages.

Goolcharran et al., "Chemical Pathways of Peptide and Protein Degradation," Department of Pharmaceutical Chemistry, The University of Kansas, Chapter 5, First published 2000—ISBN 0-203-48418-5 Master e-book ISBN, ISBN 0-203-79242-4 (Adobe eReader Format), ISBN 0-748-40745-6 (Print Edition)—23 pages.

European Pharmacopoeia, 5.0, Section 2.2.3 Potentiomatric determination of pH—2 pages.

Geppi et al., "Solid-State NMR Studies of Pharmaceutical Systems," (2008): Applied Spectroscopy Reviews, 43.3, pp. 202 and 250-252.

Highlights of Prescribing Information—CUBICIN; CUBICIN (daptomycin for injection), for Intravenous Use Initial U.S. Approval: 2003—31 pages.

Highlights of Prescribing Information—CUBICIN RF; CUBICIN RF (daptomycin for injection), for Intravenous Use Initial U.S. Approval: 2003—36 pages.

International Search Report—PCT/US2021/021887 dated Jun. 25, 2021—6 pages.

Written Opinion of the International Searching Authority—PCT/US2021/021887 dated Jun. 25, 2021—8 pages.

\* cited by examiner

| UPLC Test Method for Assay and Impurities ||
|---|---|
| Analytical Column: | Waters Acquity UPLC BEH130 C18, 2.1 mm x 300 mm, 1.7 µm, Part No. 186005792 |
| Mobile Phase A: | 29 mM KH2PO4 |
| Mobile Phase B: | 29 mM KH2PO4/Acetonitrile 4:6 |
| Separation Mode: | Isocratic, Mobile Phase A: Mobile Phase B 41:59 |
| Injection Volume: | 3 µL |
| Autosampler Temperature: | Set to 5 °C |
| Column Temperature: | 45 °C |
| Detection Wavelength: | 222 nm |
| Flow Rate: | 0.3 mL/min |
| Run Time: | 50 minutes |
| Needle Wash: | 90:10 water/Acetonitrile |
| Pump Seal Wash: | 90:10 water/Acetonitrile |

FIG. 3

Formulation for the Excipient Study II

| Formulation | API Concentration (mg/mL) | Lactose Concentration (%) | Mannitol Concentration (%) |
|---|---|---|---|
| B1 | 105 | 0 | 5 |
| B2 | 105 | 20 | 0 |
| B3 | 105 | 5 | 5 |
| B4 | 105 | 2.5 | 5 |
| B5 | 105 | 1.0 | 0 |
| B6 | 105 | 5 | 0 |

| Formulation | API Concentration (mg/mL) | Sorbitol Concentration (%) | Mannitol Concentration (%) |
|---|---|---|---|
| B7 | 105 | 5 | 5 |
| B8 | 105 | 2.5 | 5 |
| B9 | 105 | 5 | 0 |
| B10 | 105 | 20 | 0 |

| Formulation | API Concentration (mg/mL) | Captisol® Concentration (%) | Mannitol Concentration (%) |
|---|---|---|---|
| B11 | 105 | 2.5 | 0 |
| B12 | 105 | 10 | 0 |
| B13 | 105 | 20 | 0 |

FIG. 5A

Impurity D7

| % D7 | T0 | 1M 25 °C | 2M 25 °C | 3M 25 °C | 6M 25 °C | Change from T0 |
|---|---|---|---|---|---|---|
| Control | 0.53 | 1.26 | 1.58 | 1.83 | 2.35 | 1.82 |
| B1 | 0.15 | 0.61 | 0.79 | 0.83 | 1.24 | 1.09 |
| B3 | 0.10 | 0.21 | 0.26 | N/A | N/A | N/A |
| B4 | 0.13 | 0.35 | 0.46 | N/A | N/A | N/A |
| B5 | 0.15 | 0.37 | 0.46 | N/A | N/A | N/A |
| B6 | 0.19 | 0.52 | 0.66 | N/A | N/A | N/A |
| B7 | 0.09 | 0.14 | 0.16 | 0.18 | 0.28 | 0.19 |
| B8 | 0.10 | 0.18 | 0.22 | 0.24 | 0.42 | 0.32 |
| B9 | 0.09 | 0.20 | 0.27 | 0.29 | 0.42 | 0.33 |
| B10 | 0.08 | 0.32 | 0.55 | N/A | N/A | N/A |
| B11 | 0.47 | 1.40 | 1.79 | N/A | N/A | N/A |
| B12 | 0.52 | 1.62 | 2.00 | N/A | N/A | N/A |
| B13 | 0.50 | 1.60 | 2.00 | N/A | N/A | N/A |

FIG. 5B

Daptomycin Test Articles

| Formulation | Daptomycin Concentration (mg/mL) | Sorbitol Concentration (%) | Mannitol Concentration (%) | Target pH |
|---|---|---|---|---|
| DR500-63 | 105 | 5 | 5 | 6.3 |
| DR500-68 | 105 | 5 | 5 | 6.8 |
| DR500-73 | 105 | 5 | 5 | 7.3 |
| DR500HH-68 | 105 | 6 | 6 | 6.8 |
| DR500LL-68 | 105 | 4 | 4 | 6.8 |
| DR500HL-68 | 105 | 6 | 4 | 6.8 |
| DR500LH-68 | 105 | 4 | 6 | 6.8 |

FIG. 7

Impurity D7 (% Area)

| Months of Storage | | Initial pH/Test Article | | | | | | |
|---|---|---|---|---|---|---|---|---|
| | | 6.3 | 6.8 | 7.3 | HH | LL | HL | LH |
| Pre-Lyo Tank | | 0.04 | 0.04 | 0.04 | 0.05 | 0.05 | NMT 0.05 | 0.04 |
| 25 °C | 0 | 0.05 | 0.06 | 0.09 | 0.08 | 0.09 | 0.06 | 0.12 |
| | 1 | 0.06 | 0.09 | 0.14 | 0.12 | 0.14 | 0.08 | 0.21 |
| | 2 | 0.07 | 0.11 | 0.18 | 0.16 | 0.16 | 0.11 | 0.28 |
| | 3 | 0.08 | 0.13 | 0.22 | 0.19 | 0.18 | 0.13 | 0.35 |
| | 6 | 0.10 | 0.21 | 0.32 | 0.33 | 0.26 | 0.20 | 0.49 |
| | 12 | 0.19 | 0.34 | 0.54 | 0.64 | 0.39 | 0.37 | 0.75 |
| Change from T0 | | 0.14 | 0.28 | 0.45 | 0.56 | 0.30 | 0.31 | 0.63 |

FIG. 8

| Sample | Target Moisture Level (%) | Average Moisture Level (%) | Standard Deviation |
|---|---|---|---|
| EOP | 5.0 | 4.30 | 0.74 |
| 16C | 2.5 | 2.44 | 0.25 |
| 30C | 1.0 | 1.17 | 0.09 |
| 40C | 0.5 | 0.70 | 0.08 |
| 50C | 0.1 | 0.20 | 0.02 |

FIG. 9

| Sample Avg. Moisture | Parameter | T0 | 1 Month | 12 Months 25 °C |
|---|---|---|---|---|
| 4.30% | KF %H2O | 4.77 | 5.00 | 4.45 |
| | NIR %H2O | 5.01 | 4.13 | N/A |
| | Difference | -0.24 | 0.87 | N/A |
| 2.44% | KF %H2O | 2.91 | 3.08 | 2.95 |
| | NIR %H2O | 2.34 | 2.97 | N/A |
| | Difference | 0.57 | 0.11 | N/A |
| 1.17% | KF %H2O | 1.49 | 1.43 | 1.72 |
| | NIR %H2O | 1.21 | 1.11 | N/A |
| | Difference | 0.28 | 0.32 | N/A |
| 0.70% | KF %H2O | 0.70 | 0.68 | 0.77 |
| | NIR %H2O | 0.58 | 0.66 | N/A |
| | Difference | 0.12 | 0.02 | N/A |
| 0.20% | KF %H2O | 0.12 | 0.12 | 0.18 |
| | NIR %H2O | 0.2 | 0.21 | N/A |
| | Difference | -0.08 | -0.09 | N/A |

FIG. 10

| Impurity | Units | Sample Avg. Moisture | Time 0 | 1.5M | 2M | 3M | 6M | 12M | Change from T0 |
|---|---|---|---|---|---|---|---|---|---|
| D7 | % Total Area | 4.30% | 0.06 | 0.58 | 0.81 | 1.01 | 1.91 | 3.67 | 3.61 |
| | | 2.44% | 0.05 | 0.41 | 0.54 | 0.69 | 1.19 | 2.02 | 1.97 |
| | | 1.17% | 0.06 | 0.30 | 0.41 | 0.48 | 0.78 | 1.31 | 1.25 |
| | | 0.70% | 0.08 | 0.25 | 0.30 | 0.36 | 0.54 | 0.77 | 0.69 |
| | | 0.20% | 0.20 | 0.27 | 0.30 | 0.32 | 0.39 | 0.49 | 0.29 |

FIG. 11

| Formulation | Daptomycin (mg/mL) | Sorbitol (%) | Mannitol (%) | Percent S | Percent M | Molar Ratio Drug | Molar Ratio Sugar Alcohol | Tg Midpoint (°C) |
|---|---|---|---|---|---|---|---|---|
| N1 | 105 | 0.0 | 1.5 | 0% | 100% | 1 | 1.3 | N/A |
| N2 | 105 | 0.0 | 5.9 | 0% | 100% | 1 | 5.0 | N/A |
| N3 | 105 | 0.0 | 10.0 | 0% | 100% | 1 | 8.5 | N/A |
| N4 | 105 | 0.0 | 15.4 | 0% | 100% | 1 | 13.0 | N/A |
| N5 | 105 | 0.5 | 1.1 | 30% | 70% | 1 | 1.3 | 50.65 |
| N6 | 105 | 1.8 | 4.1 | 30% | 70% | 1 | 5.0 | 54.34 |
| N7 | 105 | 3.0 | 7.0 | 30% | 70% | 1 | 8.5 | 50.64 |
| N8 | 105 | 4.6 | 10.7 | 30% | 70% | 1 | 13.0 | 52.76 |
| N9 | 105 | 0.8 | 0.8 | 50% | 50% | 1 | 1.3 | 54.51 |
| N10 | 105 | 3.0 | 3.0 | 50% | 50% | 1 | 5.0 | 53.58 |
| N11 | 105 | 5.0 | 5.0 | 50% | 50% | 1 | 8.5 | 40.88 |
| N12 | 105 | 7.7 | 7.7 | 50% | 50% | 1 | 13.0 | 22.38 |
| N13 | 105 | 1.1 | 0.5 | 70% | 30% | 1 | 1.3 | 51.21 |
| N14 | 105 | 4.1 | 1.8 | 70% | 30% | 1 | 5.0 | 53.31 |
| N15 | 105 | 7.0 | 3.0 | 70% | 30% | 1 | 8.5 | 40.70 |
| N16 | 105 | 10.7 | 4.6 | 70% | 30% | 1 | 13.0 | 17.56 |
| N17 | 105 | 1.5 | 0.0 | 100% | 0% | 1 | 1.3 | 54.40 |
| N18 | 105 | 5.9 | 0.0 | 100% | 0% | 1 | 5.0 | 52.22 |
| N19 | 105 | 10.0 | 0.0 | 100% | 0% | 1 | 8.5 | 37.25 |
| N20 | 105 | 15.4 | 0.0 | 100% | 0% | 1 | 13.0 | 12.39 |

S = Sorbitol, M = Mannitol

FIG. 12

| Formulation | Daptomycin (mg/mL) | Sucrose (%) | Mannitol (%) | Percent | | Molar Ratio | | Tg Midpoint (°C) |
|---|---|---|---|---|---|---|---|---|
| | | | | S | M | Drug | Sugar or Sugar Alcohol | |
| N21 | 105 | 15 | 0 | 100% | 0% | 1 | 6.8 | 52.05 |
| N22 | 105 | 29 | 0 | 100% | 0% | 1 | 13.1 | N/A |
| N23 | 105 | 5 | 5 | 50% | 50% | 1 | 6.5 | 61.45 |

S = Sucrose; M = Mannitol

FIG. 13

| Formulation | Daptomycin (mg/mL) | Sorbitol (%) | Mannitol (%) | Percent | | Molar Ratio | | pH | Tg Midpoint (°C) |
|---|---|---|---|---|---|---|---|---|---|
| | | | | S | M | Drug | Sugar Alcohol | | |
| N24 | 105 | 5 | 5 | 50% | 50% | 1 | 8.5 | 4.5 | 29.97 |
| N25 | 105 | 5 | 5 | 50% | 50% | 1 | 8.5 | 8.0 | 42.61 |

S = Sorbitol; M = Mannitol

| Formulation | T0 value | 6M value | Change over 6M |
|---|---|---|---|
| Control | 0.53 | 2.35 | +1.82 |
| N2 | 0.57 | 2.00 | +1.43 |
| N10 | 0.20 | 0.51 | +0.31 |
| N11 | 0.16 | 0.43 | +0.27 |
| N18 | 0.19 | 0.60 | +0.41 |
| N21 | 0.20 | 0.50 | +0.30 |

FIG. 15

Impurity D7 (% Area)

| Formulation | T0 | 25°C | |
| --- | --- | --- | --- |
| | | 6M | ΔT0 |
| N1 | 0.51 | 1.78 | 1.27 |
| N2 | 0.57 | 2.00 | 1.43 |
| N3 | 0.57 | 1.97 | 1.40 |
| N4 | 0.54 | 1.98 | 1.44 |
| N5 | 0.44 | 1.56 | 1.12 |
| N6 | 0.21 | 0.57 | 0.36 |
| N7 | 0.29 | 0.94 | 0.65 |
| N8 | 0.25 | 0.73 | 0.48 |
| N9 | 0.45 | 1.57 | 1.12 |
| N10 | 0.20 | 0.51 | 0.31 |
| N11 | 0.16 | 0.43 | 0.27 |
| N12 | 0.21 | 1.49 | 1.28 |
| N13 | 0.46 | 1.57 | 1.11 |
| N14 | 0.21 | 0.54 | 0.33 |
| N15 | 0.17 | 0.49 | 0.32 |
| N16 | 0.21 | 1.62 | 1.41 |
| N17 | 0.51 | 1.61 | 1.10 |
| N18 | 0.19 | 0.60 | 0.41 |
| N19 | 0.17 | 0.60 | 0.43 |
| N20 | 0.20 | 1.78 | 1.58 |
| N21 | 0.20 | 0.50 | 0.30 |
| N22 | 0.20 | 0.82 | 0.62 |
| N23 | 0.17 | 0.47 | 0.30 |
| N24 | NMT 0.05 | 0.07 | 0.07 |
| N25 | 0.25 | 0.73 | 0.48 |

| Formulation | Change over 1M | Change over 2M | Change over 3M |
|---|---|---|---|
| N2 | 0.45 | 0.84 | 0.96 |
| N10 | 0.07 | 0.16 | 0.18 |
| N11 | 0.07 | 0.12 | 0.15 |
| N18 | 0.11 | 0.20 | 0.24 |
| N21 | 0.09 | 0.15 | 0.19 |

FIG. 17

| Formulation | % Sorbitol | % Mannitol | Molar ratio Drug | Molar ratio Polyol | Mass ratio (g) Drug | Mass ratio (g) Polyol | Mass (g) Sorbitol | Mass (g) Mannitol | Total cake Mass (g) | % Mass of Dried Cake Sorbitol | % Mass of Dried Cake Mannitol | % Mass of Dried Cake Polyol | % Mass of Dried Cake Drug |
|---|---|---|---|---|---|---|---|---|---|---|---|---|---|
| N1 | 0 | 100 | 1 | 1.3 | 0 | 1.3 | 0.525 | 0.077 | 0.000 | 0.077 | 0.602 | 0.0 | 12.8 |
| N2 | 0 | 100 | 1 | 5 | 0 | 5 | 0.525 | 0.295 | 0.000 | 0.295 | 0.820 | 0.0 | 36.0 |
| N3 | 0 | 100 | 1 | 8.5 | 0 | 8.5 | 0.525 | 0.502 | 0.000 | 0.502 | 1.027 | 0.0 | 48.9 |
| N4 | 0 | 100 | 1 | 13 | 0 | 13 | 0.525 | 0.768 | 0.000 | 0.768 | 1.293 | 0.0 | 59.4 |
| N5 | 30 | 70 | 1 | 1.3 | 0.39 | 0.91 | 0.525 | 0.077 | 0.023 | 0.054 | 0.602 | 3.8 | 8.9 |
| N6 | 30 | 70 | 1 | 5 | 1.5 | 3.5 | 0.525 | 0.295 | 0.089 | 0.207 | 0.820 | 10.8 | 25.2 |
| N7 | 30 | 70 | 1 | 8.5 | 2.55 | 5.95 | 0.525 | 0.502 | 0.151 | 0.351 | 1.027 | 14.7 | 34.2 |
| N8 | 30 | 70 | 1 | 13 | 3.9 | 9.1 | 0.525 | 0.768 | 0.230 | 0.537 | 1.293 | 17.8 | 41.6 |
| N9 | 50 | 50 | 1 | 1.3 | 0.65 | 0.65 | 0.525 | 0.077 | 0.038 | 0.038 | 0.602 | 6.4 | 6.4 |
| N10 | 50 | 50 | 1 | 5 | 2.5 | 2.5 | 0.525 | 0.295 | 0.148 | 0.148 | 0.820 | 18.0 | 18.0 |
| N11 | 50 | 50 | 1 | 8.5 | 4.25 | 4.25 | 0.525 | 0.502 | 0.251 | 0.251 | 1.027 | 24.4 | 24.4 |
| N12 | 50 | 50 | 1 | 13 | 6.5 | 6.5 | 0.525 | 0.768 | 0.384 | 0.384 | 1.293 | 29.7 | 29.7 |
| N13 | 70 | 30 | 1 | 1.3 | 0.91 | 0.39 | 0.525 | 0.077 | 0.054 | 0.023 | 0.602 | 8.9 | 3.8 |
| N14 | 70 | 30 | 1 | 5 | 3.5 | 1.5 | 0.525 | 0.295 | 0.207 | 0.089 | 0.820 | 25.2 | 10.8 |
| N15 | 70 | 30 | 1 | 8.5 | 5.95 | 2.55 | 0.525 | 0.502 | 0.351 | 0.151 | 1.027 | 34.2 | 14.7 |
| N16 | 70 | 30 | 1 | 13 | 9.1 | 3.9 | 0.525 | 0.768 | 0.537 | 0.230 | 1.293 | 41.6 | 17.8 |
| N17 | 100 | 0 | 1 | 1.3 | 1.3 | 0 | 0.525 | 0.077 | 0.077 | 0.000 | 0.602 | 12.8 | 0.0 |
| N18 | 100 | 0 | 1 | 5 | 5 | 0 | 0.525 | 0.295 | 0.295 | 0.000 | 0.820 | 36.0 | 0.0 |
| N19 | 100 | 0 | 1 | 8.5 | 8.5 | 0 | 0.525 | 0.502 | 0.502 | 0.000 | 1.027 | 48.9 | 0.0 |
| N20 | 100 | 0 | 1 | 13 | 13 | 0 | 0.525 | 0.768 | 0.768 | 0.000 | 1.293 | 59.4 | 0.0 |

FIG. 18

| Months of 25 °C Storage | Batch 1 | | Batch 2 | | Batch 3 | |
|---|---|---|---|---|---|---|
| | % D7 | % Total Impurities | % D7 | % Total Impurities | % D7 | % Total Impurities |
| 0 | 0.10 | 2.49 | 0.07 | 2.40 | 0.08 | 2.39 |
| 3 | 0.24 | 2.62 | 0.19 | 2.63 | 0.22 | 2.54 |
| 6 | 0.31 | 2.62 | 0.26 | 3.15 | 0.27 | 2.57 |
| 9 | 0.41 | 3.53 | 0.33 | 3.33 | 0.38 | 3.37 |
| 12 | 0.45 | 3.31 | 0.38 | 3.19 | 0.38 | 2.99 |
| 18 | 0.60 | 3.18 | 0.52 | 3.12 | 0.52 | 3.11 |

FIG. 19

DAPTOMYCIN FORMULATIONS CONTAINING A COMBINATION OF SORBITOL AND MANNITOL

PRIORITY CLAIM

This application claims priority to and the benefit of U.S. Provisional Patent Application Ser. No. 62/988,734, filed Mar. 12, 2020, entitled "DAPTOMYCIN FORMULATIONS CONTAINING A COMBINATION OF SORBITOL AND MANNITOL" and U.S. Provisional Patent Application Ser. No. 63/083,434, filed Sep. 25, 2020, entitled "DAPTOMYCIN FORMULATIONS CONTAINING A COMBINATION OF SORBITOL AND MANNITOL," the entire contents of each of which are hereby incorporated by reference and relied upon.

TECHNICAL FIELD

The present disclosure generally relates to daptomycin formulations containing a combination of sorbitol and mannitol and methods for making and using such formulations.

BACKGROUND

Daptomycin (FIG. 1) is a lipopeptide antibiotic used in the treatment of systemic and life-threatening infections caused by Gram-positive organisms, including vancomycin-resistant enterococci, methicillin-resistant *Staphylococcus aureus*, and penicillin-resistant *Streptococcus pneumoniae*. Daptomycin is a naturally occurring compound found in the soil saprotroph *Streptomyces roseosporus*. The compound can be provided as a lyophilized cake that can be reconstituted with sterile water and then administered intravenously.

The consensus in the art is that sucrose is the preferred excipient for enhancing chemical stability of lyophilized daptomycin during storage; and although polyols such as mannitol can be used in combination with sucrose, a polyol such as mannitol by itself (without sucrose) is not thought to enhance chemical stability of lyophilized daptomycin as effectively as sucrose.

SUMMARY

As set forth in the experimental examples disclosed later herein, the present inventors surprisingly found that a combination of sorbitol and mannitol, particularly at specific weight percentages thereof and specific molar weight ratios relative to the daptomycin, can be used to provide an advantageous daptomycin product that can be effectively stored above room temperature, e.g., at about 25° C. for at least one month, for example at about 25° C. for at least six months. Moreover, after such storage, daptomycin formulations that include the combination of sorbitol and mannitol as disclosed herein can unexpectedly have daptomycin stability that is substantially similar to daptomycin formulations containing the typically preferred excipient (sucrose), as measured by formation of the primary daptomycin impurity, Impurity D7 (FIG. 2).

These results are unexpected because the common understanding is that sorbitol should be avoided in such formulations due to the relatively low $T_g'$ value of sorbitol; but to the contrary, the inventors found that the sorbitol-containing formulation surprisingly could be quickly and effectively freeze-dried despite the relatively low $T_g'$ value. For example, "Lyophilization of Biopharmaceuticals" by Springer Science & Business Media, 2004, edited by Costantino and Pikal, discloses that lyophilisation of excipients with a very low $T_g'$, such as sorbitol, should be avoided due to a tendency to promote cake collapse. However, the inventors found the $T_g'$ values of daptomycin formulations containing the combination of sorbitol and mannitol are very low (approximately −40° C.) but did not affect the manufacturability of the formulations.

Further in this regard, the inventors unexpectedly found that daptomycin formulations containing the combination of sorbitol and mannitol could be freeze-dried without substantial stability loss at higher temperatures than would be expected. Consequently, these inventive daptomycin formulations can be freeze-dried quickly and effectively (e.g., without cake collapse) in less than one week, for example in about 48 hours or less. For example, in a particular non-limiting embodiment, a daptomycin formulation containing the combination of sorbitol and mannitol was freeze-dried into a stable cake by a drying process comprising a sublimation drying at a temperature of about −25° C. to about 50° C. for a time period of about 15 hours to about 120 hours, preferably about 5° C. to about 30° C. for about 16 hours to about 25 hours, more preferably about 8° C. to about 25° C. for about 17 hours to about 30 hours, even more preferably about 10° C. to about 20° C. for about 18 hours to about 25 hours, most preferably about 15° C. for about 20 hours, optionally preceded and/or followed by one or more additional drying steps.

This result was surprising because the very low $T_g'$ of sorbitol would have suggested an inefficient, commercially impractical drying time for such a formulation. This unexpected manufacturability of a daptomycin formulation provided by its combination of sorbitol and mannitol advantageously allows a commercially cost-effective drying process and a beneficial stability of the daptomycin cake. Indeed, a freeze-drying temperature above the $T_g'$ of sorbitol would have been expected to collapse the daptomycin cake.

Moreover, sorbitol is an isomer of mannitol and thus has a chemical structure similar to that of mannitol. Therefore, these results are also surprising because it would not have been expected that the combination of sorbitol and mannitol would achieve stability approximately equal to that obtained by sucrose, which cannot be achieved by mannitol by itself.

Further in this regard, the combinations of sorbitol and mannitol as disclosed herein surprisingly reduced the amount of Impurity D7 arising from storage at about 25° C. compared to would be expected for the combination based on their effect individually, thus achieving an unexpected level of stability for the daptomycin, as measured as set forth in FIG. 3 and discussed in greater detail later herein. Impurity D7 is the main impurity that grows in the lyophilized cake of daptomycin, and the combination of sorbitol and mannitol can prevent D7 formation during storage to a substantially similar extent relative to daptomycin formulations containing the typically preferred excipient, sucrose.

Therefore, an aspect of the present disclosure is a solid daptomycin formulation that includes a combination of sorbitol and mannitol and has an increase in Impurity D7 no greater than about 1.00% after storage at 25° C. for 6 months, for example an increase in Impurity D7 no greater than about 0.90% after storage at 25° C. for 6 months or no greater than about 0.80% after storage at 25° C. for 6 months, preferably an increase in Impurity D7 no greater than about 0.70% after storage at 25° C. for 6 months, more preferably an increase in Impurity D7 no greater than about 0.60% after storage at 25° C. for 6 months, even more preferably an increase in Impurity D7 no greater than about 0.50% after storage at 25° C. for 6 months, yet more preferably an increase in Impurity D7 no greater than about 0.40% after storage at 25° C. for 6 months, most preferably an increase in Impurity D7 no greater than about 0.30% after storage at 25° C. for 6 months, as measured as set forth in FIG. 3.

In an aspect of the present disclosure, a method of manufacture of a pharmaceutically acceptable solid composition comprising daptomycin is provided. The method comprises drying an aqueous solution comprising (i) water, (ii) the daptomycin, (iii) sorbitol in an amount of about 3.0 wt. % to about 6.0 wt. % of total volume of the aqueous solution and (iv) mannitol in an amount of about 3.0 wt. % to about 5.0 wt. % of the total volume of the aqueous solution to form the solid composition with a moisture content of about 1.0 wt. % or less of total weight of the solid composition. The resultant solid composition is another aspect of the present disclosure.

In another aspect of the present disclosure, a pharmaceutically acceptable solid composition comprising daptomycin is provided. The pharmaceutically acceptable solid composition comprises the daptomycin and a combination of sorbitol and mannitol. In some embodiments, the sorbitol is preferably about 6.2 wt. % to about 45.3 wt. % of total weight of the solid composition, the mannitol is about 3.1 wt. % to about 47.5 wt. % of the total weight of the solid composition, and the total of the sorbitol and the mannitol is preferably about 31.0 wt. % to about 59.4 wt. % of the total weight of the solid composition.

In yet another aspect of the present disclosure, a method of treating a bacterial infection in a subject having the bacterial infection is provided. The method comprises administering an effective amount of a pharmaceutical product to the subject; the pharmaceutical product comprises daptomycin and a combination of mannitol and sorbitol.

BRIEF DESCRIPTION OF THE DRAWINGS

FIG. 3 shows the methodology for determining the amount of daptomycin impurity D7.

FIGS. 5A and 5B show the test articles and the results of the experimental study in Example 1A disclosed herein.

FIGS. 7 and 8 show the test articles and the results of the experimental study in Example 2 disclosed herein.

FIGS. 9-11 show the test articles and the results of the experimental study in Example 3 disclosed herein.

FIGS. 12-17 show the test articles and the results of the experimental study in Example 4 disclosed herein.

FIG. 18 is a table showing some of the test articles from Example 4 which limited the increase in Impurity D7 after storage at 25° C. for 6 months to an increase no greater than about 1.00% relative to the amount at the beginning of storage. The table also shows embodiments reasonably interpolated from these test articles to likewise limit the increase in Impurity D7 after storage at 25° C. for 6 months to an increase no greater than about 1.00%. The table includes component amounts calculated for the solid cake (these calculations exclude moisture, which is up to about 1.0 wt. % of the solid cake).

FIG. 19 is a table showing results for impurity D7 and total impurities from the study in Example 5 which investigated 18 months of long-term data (25° C. storage) for three batches of daptomycin formulation N11, which is representative of an embodiment provided by the present disclosure.

DETAILED DESCRIPTION

Definitions

Figure 1:
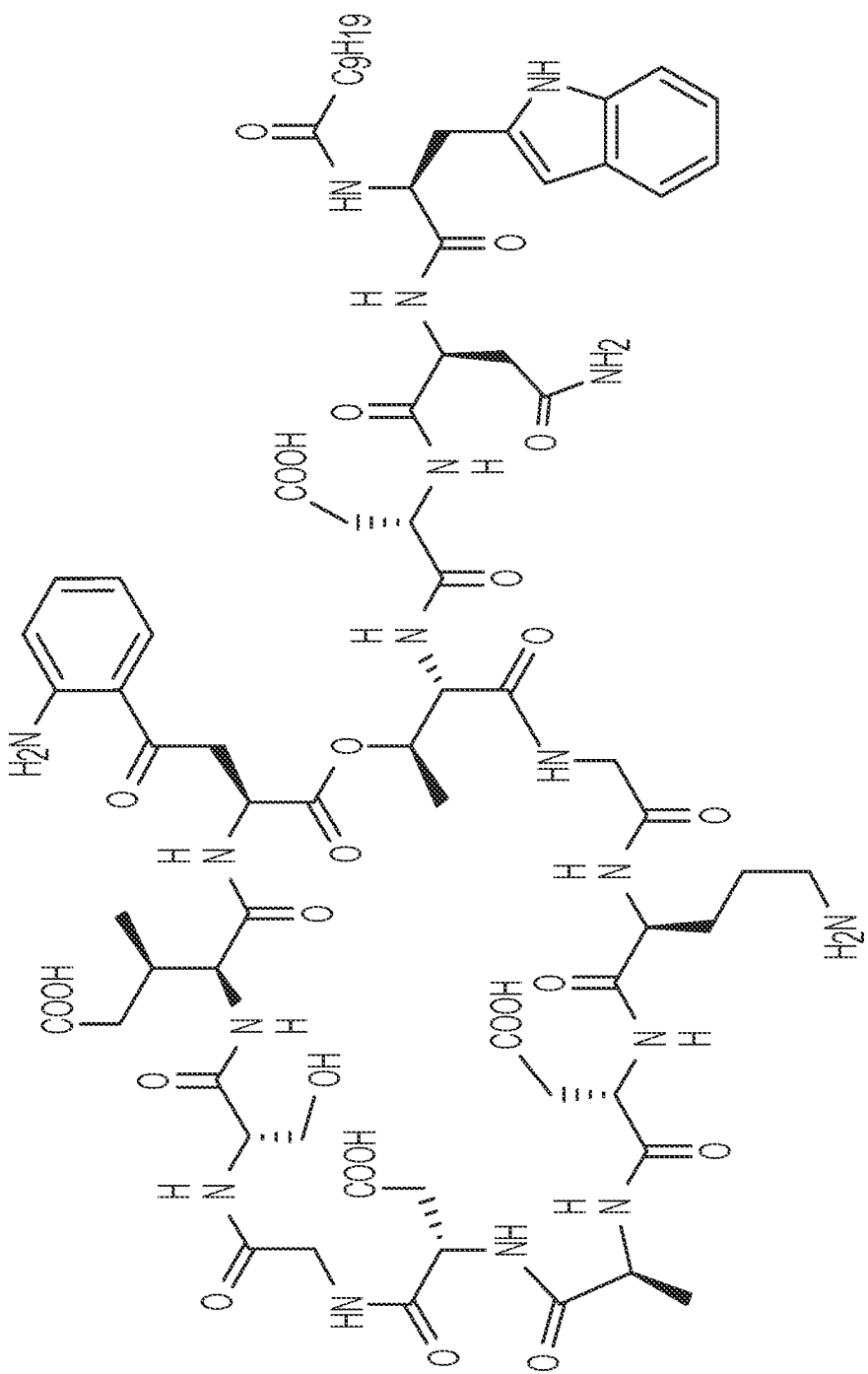
FIG. 1 shows the chemical structure for daptomycin.
Figure 2:
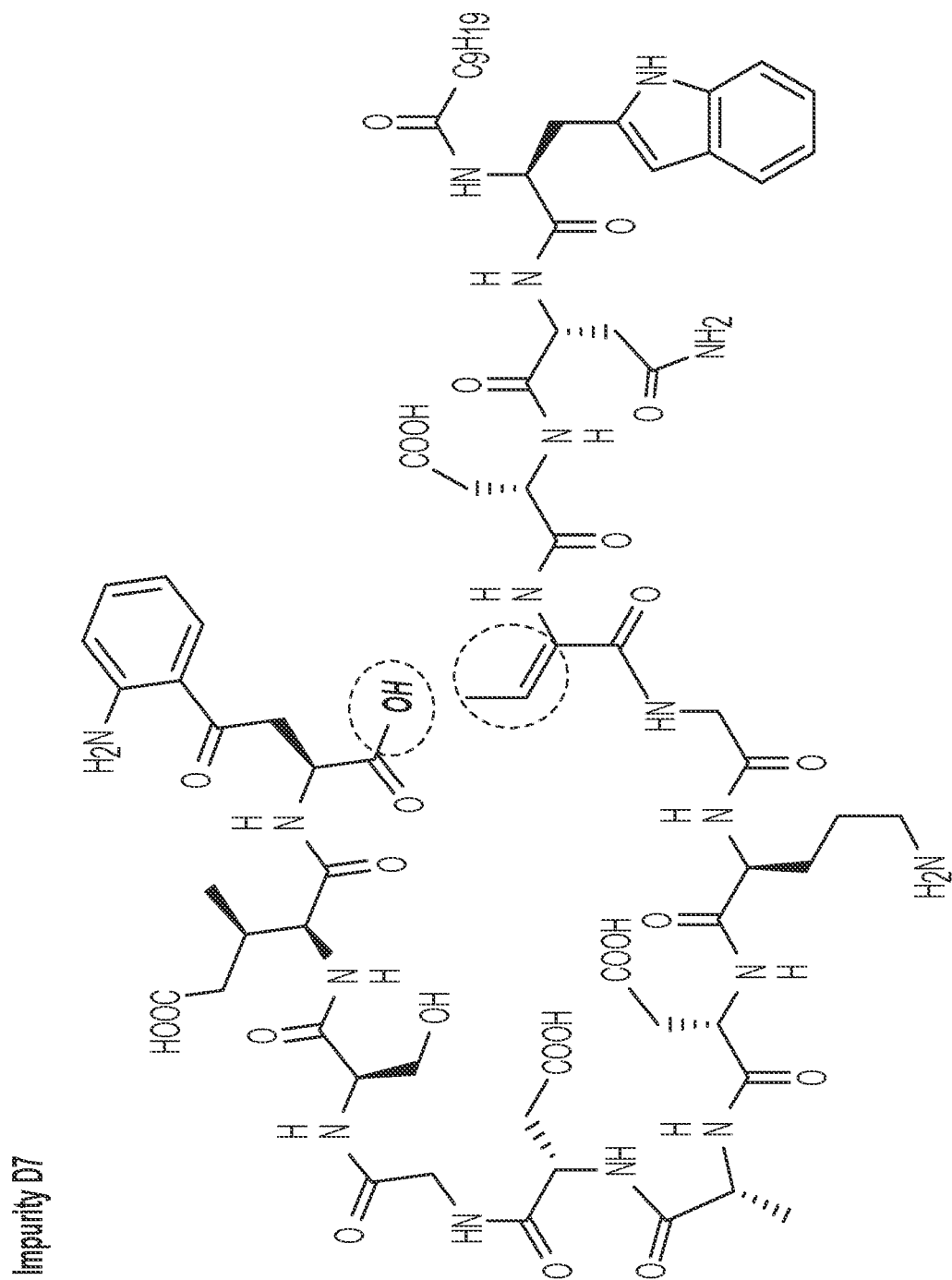
FIG. 2 shows the chemical structure for daptomycin impurity D7.

Some definitions are provided hereafter. Nevertheless, definitions may be located in the "Embodiments" section below, and the above header "Definitions" does not mean that such disclosures in the "Embodiments" section are not definitions.

Weight percentages expressed herein for a solid composition are by weight of the referenced component relative to the total weight of the solid composition unless expressed otherwise. For example, a component that is 3.0 wt. % of a solid composition is equivalent to 3.0 g of the component/100 g of the total solid composition. Weight percentages expressed herein for an aqueous composition are by weight of the referenced component relative to the total volume of the aqueous composition unless expressed otherwise. For example, a component that is 3.0 wt. % of an aqueous composition is equivalent to 3.0 g of the component/100 mL of the total aqueous composition.

When reference herein is made to the pH, values correspond to pH measured at 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, even more preferably −0.1% to +0.1% of the referenced number, most preferably −0.01% to +0.01% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a temperature" or "the temperature" includes two or more temperatures.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

A "subject" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form", as used herein, refers to physically discrete units suitable as unitary dosages for human and animal subjects, each unit containing a predetermined quantity of the composition disclosed herein in an amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

The term "pharmaceutically acceptable" as used herein refers to substances that do not cause substantial adverse allergic or immunological reactions when administered to a subject.

The term "substantially no" as used in reference to a particular component means that any of the component present constitutes less than about 2.0% by weight, such as less than about 1.0% by weight, preferably less than about 0.5% by weight or, more preferably, less than about 0.1% by weight.

The term Tg refers to the glass transition temperature of a composition in a dried state, typically influenced by both internal moisture content and formulation, and the term Tg' (Tg-prime) refers to the glass transition temperature of a composition in a freeze-concentrated state, typically influenced solely by formulation.

Unless otherwise indicated, the amount of daptomycin and structurally similar compounds such as Impurity D7 was measured using Ultra Performance Liquid Chromatography (UPLC) analysis in aqueous reconstituted liquid solutions containing daptomycin, using an Agilent 1290 or Waters H class ultra high performance liquid chromatography instrument with an ultraviolet (UV) detector. Peak areas were measured using Waters Empower 3 software. Unless otherwise noted, the purity of a solid daptomycin preparation was determined by reconstituting 500 mg of the solid daptomycin preparation in 10 mL of water to form a reconstituted solution, then measuring the absorbance of the reconstituted sample at 222 nm by UPLC using the parameters described in FIG. 3. The Area % of daptomycin impurities (e.g., Impurity D7) were calculated using the equation below.

$$\% \text{ Individual Related Substance} = \frac{Ai}{Au + \sum Ai} \times 100$$

Where:
Ai=Adjusted Peak area response of each individual related substance in the Sample Solution.
Au=Peak area response of Daptomycin in the Sample Solution Embodiments An aspect of the present disclosure is a method of making a solid composition comprising daptomycin. The solid composition may be subsequently reconstituted in an aqueous pharmaceutically acceptable diluent (e.g., sterile and/or bacteriostatic water, preferably with 0.9 wt. % sodium chloride) to form a pharmaceutical product for parenteral administration. Non-limiting examples of parenteral administration include intravenously, intramuscularly, intraperitoneally, subcutaneously, intraarticularly, intrasynovially, intraocularly, intrathecally, topically, and inhalation. For example, the solid composition can be a lyophilized cake containing approximately 500 mg of daptomycin for intravenous administration following reconstitution with about 10 mL of approximately 0.9 wt. % sodium chloride.

Figure 4:
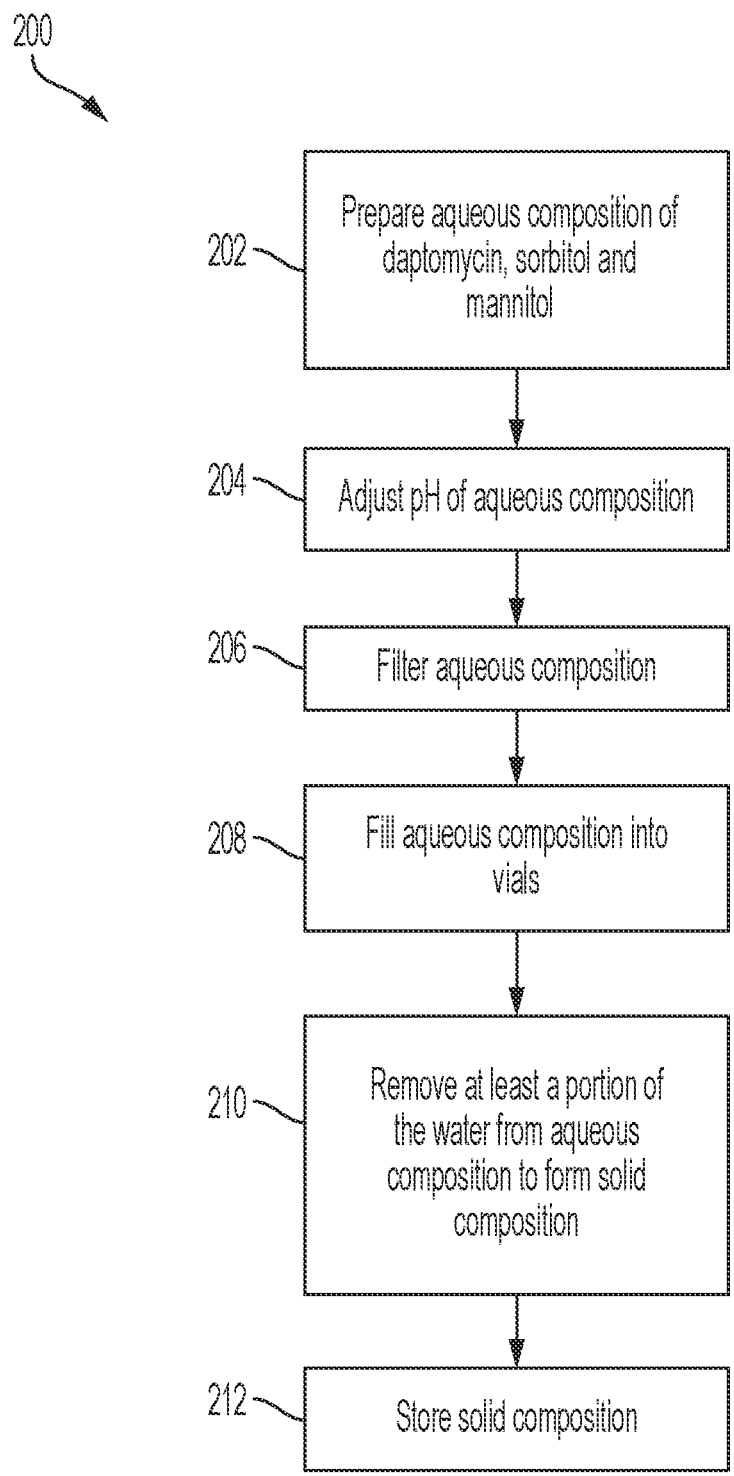
FIG. 4 is a flowchart of a non-limiting example of an embodiment of a method of making a solid composition comprising daptomycin according to the present disclosure.

FIG. 4 generally illustrates a flowchart of a non-limiting example of an embodiment of a method 200 of making a solid composition comprising daptomycin. Although some embodiments of the method 200 can include all of the depicted steps, other embodiments of the method 200 can omit one or all of the depicted steps, and each step is optional unless indicated otherwise. The present disclosure is not limited to the specific embodiment of the method 200 shown in FIG. 4.

The method of making a solid composition comprising daptomycin comprises subjecting an aqueous composition of daptomycin, sorbitol and mannitol to at least one step that removes at least a portion of the water from the aqueous composition, such as one or more of lyophilization, freeze-drying, spray-drying, fluid-bed drying, spray cooling, precipitation or crystallization (e.g., step 210 of the method 200). The terms "lyophilisation" and "freeze-drying" are used interchangeably herein. The "at least one step that removes at least a portion of the water from the aqueous composition" is hereafter referred to as "the drying" step, although this term does not imply that all of the water is necessarily removed.

Moreover, the present disclosure is not limited to a specific embodiment of the drying step 210, and the drying step 210 can use any pharmaceutically acceptable process for converting a liquid composition to a solid composition having the moisture content disclosed herein. Further in this regard, the skilled person in this art will recognize that one or more parameters of the drying step can be selected based on the desired moisture content of the solid composition, for example, one or more of the time, the temperature, the pressure, or the number of stages in the drying step 210. As discussed in greater detail hereafter, a preferred moisture content of the solid composition is about 1.0 wt. % moisture or less of total weight of the solid composition, and the skilled artisan can easily determine lyophilisation conditions suitable for achieving the moisture contents disclosed herein, such as about 1.0 wt. % or less of total weight of the solid composition. The temperatures applied to the composition during the drying step 210 are referenced herein as "shelf temperature"; and the temperature of the composition itself during the drying step 210 is referenced herein as the "product temperature."

The drying step 210 preferably comprises sublimation drying that removes ice in the composition of daptomycin, sorbitol and mannitol by sublimation, optionally substantially all of the ice. Sublimation drying is sometimes known in the art as primary drying.

The product temperature is typically colder than the shelf temperature during the sublimation drying because the heat applied to the composition is being at least partially used for the sublimation phase change. When sublimation of the ice is substantially or fully complete, the product temperature will typically increase and approach the shelf temperature. Therefore, the sublimation drying disclosed herein is substantially completed when the product temperature is approximately equal to the shelf temperature; and in such embodiments, any optional drying after the completion of the sublimation drying is characterized as additional drying that is subsequent to the sublimation drying.

Further in this regard, some embodiments optionally include one or more additional drying steps subsequent to the sublimation drying. The one or more subsequent drying steps can remove water from the composition, for example water that is remaining after the sublimation drying and/or that is bound to other components of the composition. Such drying subsequent to sublimation drying is sometimes known as desorption, and the subsequent drying can be performed until the solid composition has a target moisture content, preferably a moisture content suitable for long term storage. In some embodiments, the subsequent drying is performed at a shelf temperature that is the same as or higher than the shelf temperature used for sublimation drying. Nevertheless, in some embodiments, the sublimation drying is optionally not followed by any subsequent drying.

For example, in some embodiments the sublimation drying is optionally preceded and/or followed by one or more additional drying steps, such that the drying step 210 comprises sublimation drying, optionally one or more preceding drying steps, and optionally one or more subsequent drying steps. For example, in a particular non-limiting embodiment, the sublimation drying adjusts the moisture content of the composition to a lower moisture content, and then one or more additional drying steps subsequent to the sublimation drying adjust the moisture content of the composition to the target moisture content. The sublimation drying step can subject the composition to a constant temperature and/or a plurality of different temperatures as long as each of the plurality of different temperatures are within the desired range.

For example, sublimation drying can be performed at a temperature of about −25° C. to about 50° C., preferably about 5° C. to about 30° C., more preferably about 8° C. to about 25° C., even more preferably about 10° C. to about 20° C., most preferably at about 15° C. for a time period of about 15 hours to about 120 hours, preferably about 16 hours to about 25 hours, more preferably about 17 hours to about 30 hours, even more preferably about 18 hours to about 25 hours, most preferably about 20 hours.

These temperatures are the temperatures applied to the composition ("shelf temperature," as noted above); and the temperature of the composition itself (the "product temperature," as noted above) is less than the temperatures applied to the composition during the sublimation drying, for example less than the example temperatures of sublimation drying disclosed above, and reaches about the shelf temperature at the completion of sublimation drying. In some embodiments, the product temperature is about −30° C. to about 40° C. during sublimation drying but typically not greater than the shelf temperature.

Preferably, the drying step 210 is a process selected from the group consisting of (i) the process comprises the sublimation drying, (ii) the process comprises the sublimation drying and one or more preceding drying steps, (iii) the process comprises the sublimation drying and one or more subsequent drying steps and (iv) the process comprises the sublimation drying, one or more preceding drying steps, and one or more subsequent drying steps.

In an embodiment, the aqueous composition can be frozen at a temperature equal to or less than the freezing point of the aqueous composition before performing the drying, for example by subjecting the aqueous composition to a temperature below about −14° C., such as about −40° C., for about 2 hours, before performing the drying. In such an embodiment, the product temperature will typically be less than the shelf temperature during the sublimation drying.

Preferably the solid composition is a lyophilized powder, for example in the form of a substantially homogeneous cake having a substantially uniform color (e.g., pale yellow to light brown) and a substantially uniform texture. However, the present disclosure is not limited to a specific form of the solid composition, and the form of the solid composition can be any known to be pharmaceutically acceptable by those in the art.

Preferably the aqueous solution is filtered before the drying step, for example by a filter of polyethersulfone (PES) or polyvinylidenefluoride (PVDF)) (e.g., step 206 of the method 200). The aqueous solution (filtered or unfiltered) can be filled into one or more vials (e.g., glass vials) (e.g., step 208 of the method 200) before the drying step, for example such that the drying step is performed on vials of the aqueous composition. One or more parameters of the drying step (e.g., step 210 of the method 200) can be selected based on the desired moisture content of the solid composition, for example one or more of the time, the temperature, or the pressure of the drying step.

Preferably the aqueous composition has a pH of about 4.5 to about 8.0, preferably about 6.0 to about 7.5, more preferably about 6.7 to about 7.3, most preferably about 7.0, prior to and/or during the drying step for the aqueous composition. Accordingly, some embodiments of the method comprise at least one pH adjustment step (e.g., step 204 of the method 200), for example addition of a base such as sodium hydroxide (e.g., 1N NaOH or 5N NaOH) and/or addition of an acid such as hydrochloric acid (e.g., 1N HCl). In a particular non-limiting example, the at least one pH adjustment step comprises adjusting the pH to about 6.0 using 5N sodium hydroxide, and then adjusting the pH to about 7.0 using 1N sodium hydroxide, and then, if needed, adjusting the pH down to about 7.0 using 1N hydrochloric acid if the pH is inadvertently increased too high. However, the present disclosure is not limited to a specific embodiment of the optional pH adjustment step, and the optional pH adjustment step can be any known to be pharmaceutically acceptable by those in the art.

Non-limiting examples of the aqueous composition can comprise the daptomycin in an amount of about 80 to about 130 mg/mL, preferably about 90 to about 120 mg/mL, more preferably about 100 to about 110 mg/mL, most preferably about 105 mg/mL. Further in this regard, non-limiting examples of the aqueous composition can comprise the daptomycin in an amount of about 8.0 to about 13.0 wt. %, preferably about 9.0 to about 12.0 wt. %, more preferably about 10.0 to about 11.0 wt. %, most preferably about 10.5 wt. % of total volume of the aqueous composition.

In some embodiments, the method comprises preparing the aqueous composition (e.g., step 202 of the method 200) before the aqueous composition is subjected to the drying step. For example, the method can comprise addition of the daptomycin to the liquid (e.g., pure water and/or ultrapure water) and, after the daptomycin is dissolved, addition of the sorbitol and the mannitol to the liquid that already contains the dissolved daptomycin. In a preferred embodiment, the method comprises addition of the sorbitol and the mannitol to the liquid (e.g., pure water and/or ultrapure water) and, after the sorbitol and the mannitol are dissolved, addition of the daptomycin to the liquid that already contains the dissolved sorbitol and the dissolved mannitol. In another preferred embodiment, the method comprises dry mixing the daptomycin, the sorbitol, and the mannitol together and then adding the dry mixture to the liquid (e.g., pure water and/or ultrapure water). However, the present disclosure is not limited to a specific process by which the aqueous composition is prepared, and the process by which the aqueous composition is prepared can be any known to be pharmaceutically acceptable by those in the art.

At least a portion of these steps of preparing the aqueous composition can optionally be performed at about 2° C. to about 8° C., for example approximately 5° C. or, additionally or alternatively, at ambient conditions, i.e., a temperature of about 25° C. and a pressure of about 1 atm. Preferably the mixing is performed with constant agitation, for example at least about 15 minutes of agitation for each mixing step.

As noted above, the aqueous composition comprises a combination of sorbitol and mannitol. Non-limiting examples of the aqueous composition can comprise the sorbitol in an amount of about 1.2% to about 9.0% by weight, preferably about 3.5% to about 5.5% by weight, more preferably about 4.0% to about 5.0% by weight, even more preferably about 4.5% to about 5.0% by weight, most preferably about 5.0% by weight, relative to total volume of the aqueous composition. Non-limiting examples of the aqueous composition can comprise the mannitol in an amount of about 0.6% to about 9.5% by weight, preferably about 3.5% to about 5.0% by weight, more preferably about 4.0% to about 5.0% by weight, even more preferably about 4.5% to about 5.0% by weight, most preferably about 5.0% by weight, relative to total volume of the aqueous composition.

Some embodiments of the aqueous solution used in the method can have a daptomycin:(sorbitol+mannitol) molar ratio from about 1:4 to about 1:13, preferably from about 1:5 to about 1:13, and a sorbitol:mannitol weight ratio from 20:80 to 40:60, for example about 30:70.

Other embodiments of the aqueous solution used in the method can have a daptomycin:(sorbitol+mannitol) molar ratio from about 1:4 to about 1:9, preferably from about 1:5 to about 1:8.5, and a sorbitol:mannitol weight ratio above 40:60 up to 90:10, preferably above 40:60 up to about 80:20, more preferably about 50:50 to about 70:30, for example about 50:50, about 60:40, or about 70.30.

In some embodiments, the aqueous composition can consist essentially of (or consist of) the daptomycin, the combination of sorbitol and mannitol, sterile water, optionally a pH-adjusting agent such as sodium hydroxide and/or hydrochloric acid, and optionally a buffering agent such as one or more of citrate, histidine, phosphate, tryptophan, maleate, or carbonate. Further in this regard, some embodiments of the aqueous composition comprise a buffering agent, but preferred embodiments contain substantially no buffering agent.

Preferably the aqueous composition contains substantially no sugars and/or contains substantially no other polyols additional to the sorbitol and the mannitol, and in some embodiments the sorbitol and the mannitol are the only polyols in the aqueous composition.

After the drying of the aqueous composition into the solid composition, the method can further comprise storing the solid composition (e.g., step 212 of the method 200). For example, the solid composition can be stored for a time period of about 1 month to about 24 months at a temperature of about 25° C. to about 30° C. or a time period of about 1 week to about 2 weeks at a temperature of about 40° C. For example, the method can further comprise storing the solid composition for a time period of about 6 months at a temperature of about 25° C. The storage can include exposure to light, and the characteristics of the solid compositions disclosed herein can be substantially unchanged by such light exposure (e.g., appearance, reconstitution time, color, pH, daptomycin concentration, and/or impurities).

After the storage, the solid composition can be reconstituted and administered parenterally. For example, the solid composition can be reconstituted into a parenterally administrable pharmaceutical product having a daptomycin concentration of about 25 mg/mL to about 200 mg/mL. Preferably, about 500 mg of the solid composition dissolves in about 10 mL of sterile water or bacteriostatic water in about 2 minutes or less at 25° C., and/or about 350 mg of the solid composition dissolves in about 10 mL of sterile water or bacteriostatic water in about 1 minute or less at 25° C.

Another aspect of the present disclosure is a solid composition comprising daptomycin and a combination of sorbitol and mannitol; as a non-limiting example, the solid composition obtained by any of the methods disclosed above. In some embodiments, the solid composition can have a moisture content not greater than about 1.0% of total weight of the solid composition, preferably not greater than about 0.9% of total weight of the solid composition, more preferably not greater than about 0.8% of total weight of the solid composition, even more preferably not greater than about 0.7% of total weight of the solid composition, most preferably not greater than about 0.5% of total weight of the solid composition, for example not greater than about 0.2% of total weight of the solid composition or not greater than about 0.1% of total weight of the solid composition.

Preferably, the solid composition is in a unit dosage form such as a lyophilized cake, and the unit dosage form can comprise about 350 mg to about 600 mg of the daptomycin, preferably about 450 mg to about 550 mg of the daptomycin, more preferably about 475 mg to about 525 mg of the daptomycin, most preferably about 500 mg of the daptomycin.

In preferred embodiments of the solid composition, the sorbitol is about 6.2 wt. % to about 45.3 wt. % of total weight of the pharmaceutically acceptable solid composition, and the mannitol is about 3.1 wt. % to about 47.5 wt. % of total weight of the pharmaceutically acceptable solid composition. In these embodiments, the total of the sorbitol and the mannitol is preferably about 31.0 wt. % to about 59.4 wt. % of total weight of the pharmaceutically acceptable solid composition.

For example, some embodiments of the solid composition can have a daptomycin:(sorbitol+mannitol) molar ratio from about 1:4 to about 1:13, preferably from about 1:5 to about 1:13, and a sorbitol:mannitol weight ratio from 20:80 to 40:60, for example about 30:70. In such embodiments, the sorbitol is preferably about 6.2 wt. % to about 22.1 wt. % of total weight of the solid composition, more preferably about 9.3 wt. % to about 22.1 wt. % of total weight of the solid composition; and the mannitol is preferably about 18.6 wt. % to about 47.5 wt. % of total weight of the solid composition, more preferably about 18.6 wt. % to about 41.6 wt. % of total weight of the solid composition. In these embodiments, the total of the sorbitol and the mannitol is preferably about 31.0 wt. % to about 59.4 wt. % of total weight of the solid composition.

As another example, other embodiments of the solid composition can have a daptomycin:(sorbitol+mannitol) molar ratio from about 1:4 to about 1:9, preferably from about 1:5 to about 1:8.5, and a sorbitol:mannitol weight ratio above 40:60 up to 90:10, preferably above 40:60 up to about 80:40, more preferably about 50:50 to about 70:30, for example about 50:50, about 60:40, or about 70.30. In such embodiments, the sorbitol is preferably about 12.4 wt. % to about 45.3 wt. % of total weight of the solid composition, more preferably about 15.5 wt. % to about 35.2 wt. % of total weight of the solid composition; and the mannitol is preferably about 3.1 wt. % to about 25.2 wt. % of total weight of the solid composition, more preferably about 9.3 wt. % to about 25.2 wt. % of total weight of the solid composition. In these embodiments, the total of the sorbitol and the mannitol is preferably about 31.0 wt. % to about 50.3 wt. % of total weight of the solid composition.

In some embodiments, the solid composition consists essentially of or consists of the daptomycin, the combination of sorbitol and mannitol, residual sterile water, optionally a pH-adjusting agent such as sodium hydroxide and/or hydrochloric acid, and optionally a buffering agent such as one or more of citrate, histidine, phosphate, or tryptophan. Further in this regard, some embodiments of the solid composition comprise a buffering agent, but preferred embodiments contain substantially no buffering agent additional to the sorbitol and the mannitol.

Preferably the solid composition contains substantially no sugars and/or contains substantially no other polyols additional to the sorbitol and the mannitol, and in some embodiments the sorbitol and the mannitol are the only polyols in the solid composition.

Another aspect of the present disclosure is a method of treating a bacterial infection in a subject having the bacterial infection. The method comprises administering an effective amount of any of the compositions disclosed herein to the subject. The method can comprise reconstituting one of the solid compositions disclosed herein, preferably in a pharmaceutically acceptable diluent such as one or more of sterile water, sterile sodium chloride, or bacteriostatic water, before the administering. Non-limiting examples of bacterial infections that can be treated by the methods and compositions disclosed herein include skin and skin structure infections and blood stream infections caused by gram-positive bacteria, e.g., *Staphylococcus aureus, Streptococcus pyogenes, Streptococcus agalactiae, Streptococcus dysgalactiae* subsp. *equisimilis*, and *Enterococcus faecalis*.

EXAMPLES

The following non-limiting examples support the concept of daptomycin stabilized by the combination of mannitol and sorbitol.

Example 1A

A study examined the effect of daptomycin concentration and addition of excipients, such as mannitol, sorbitol, lactose, and sulfobutyl ether of β-cyclodextrin (SBE-β-CD), on the stability of daptomycin. In this regard, at each time, the formulations were assayed by UPLC whose conditions are described in FIG. 3.

Test articles consisted of a 10 mL or a 20 mL vial with a freeze-dried cake of 525 mg of daptomycin at pH 6.8. The concentration of API and excipients were varied between formulations. The study used sorbitol, mannitol, lactose, and SBE-13-CD (i.e., CAPTISOL®) (FIG. 5A). The vials were placed in freeze driers and lyophilized.

The glass transition temperatures of formulations B7, B8, and B9 were determined. The glass transition temperatures were 29, 37, and 38° C. respectively. It was hypothesized that the reason for the good stability at 25° C. and poor stability at 40° C. was due to the samples being above the glass transition temperature when stored at 40° C. Therefore, the samples that were to be tested at 5° C. were moved to storage at 30° C. after 1.5 months at 5° C. to see if the samples were still stable at 30° C. The stability of the 30° C. samples were equivalent to the 25° C. samples.

The SBE-β-CD samples (B11-B13) had an increase of 2% of D7 after only 2 months at 25° C. and were therefore removed from the study after 2 months. The formulations that reduced the increase in Impurity D7 the best at 25° C. were formulations B7, B8, and B9, with formulation B7 only having an increase in D7 of 0.2% (FIG. 5B).

Example 1B

A study examined formulations with sorbitol and mannitol, which were found to have very low Tg' values, and the study investigated the product temperature in the freeze dryer to determine how quickly the lyophilization cycle could be performed without substantial stability loss. Specifically, samples of formulations B7 (5% sorbitol, 5% mannitol), B8 (2.5% sorbitol, 5% mannitol), and B9 (5% sorbitol, 0% mannitol) as discussed in the preceding example (FIG. 5A) were reconstituted with 5 mL of water and allowed to dissolve. Samples were then freeze dried for product temperature runs. The cakes were observed for collapse and images were taken. The samples were then reconstituted with 5 mL's of water using a pipet with a vial open to the atmospheric pressure. The reconstitution time was recorded and images were taken if warranted.

Figure 6A:
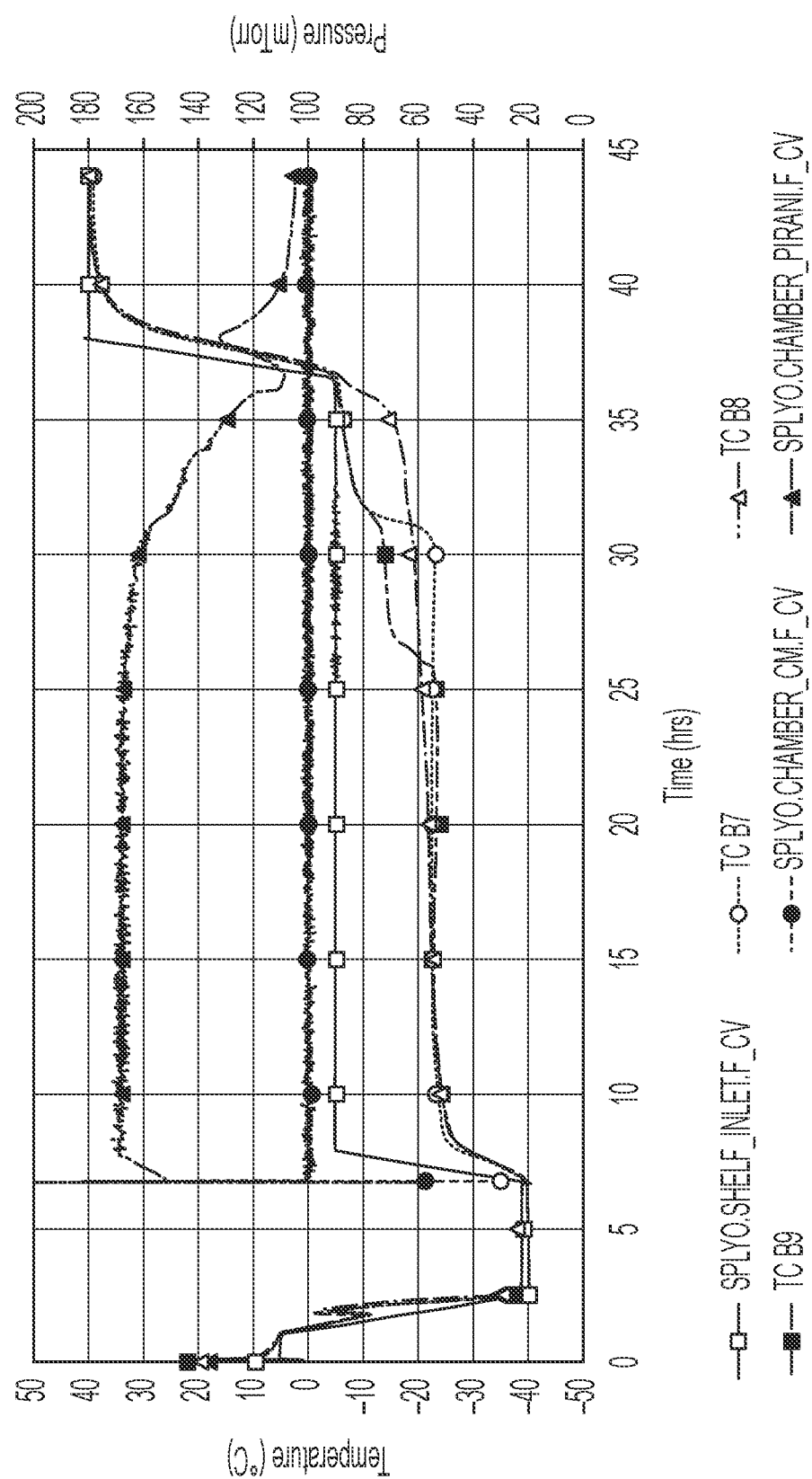
FIGS. 6A, 6B and 6C show the lyophilization cycle process parameters for the first, second and third product temperature runs in the experimental study in Example 1B disclosed herein (dark blue line is shelf temperature; orange line is chamber pressure; yellow, light blue, and green lines are product temperatures for the three formulations; and gray line is pirani reading which indicates amount of water vapor).

For the first product temperature run (FIG. 6A), the product was loaded at a shelf temperature of 5° C. and held for sixty (60) minutes; then for freezing, the shelf temperature was ramped to −40° C. at 0.5° C./min and held for four (4) hours; then for sublimation drying, a vacuum of 100 mTorr was applied and the shelf temperature was ramped to −5° C. at 0.5° C./min and held until the product temperature of all three formulations reached about −5° C. (about twenty-eight (28) hours); and then for additional drying, the shelf temperature was ramped to 40° C. at 0.5° C./min and held for 360 minutes.

The critical product temperature, which is the product temperature maintained during most of the primary drying, determined for the first product temperature run (FIG. 6A) was to −22.2° C. for formulation B7 and −23.0° C. for formulation B9. When the product temperatures were approximately −22.5° C., all formulations had acceptable cakes and no collapse was seen. The reconstitution time was approximately 2 minutes, 3 minutes and 4 minutes for formulations B7, B8, and B9 respectively.

Figure 6B:
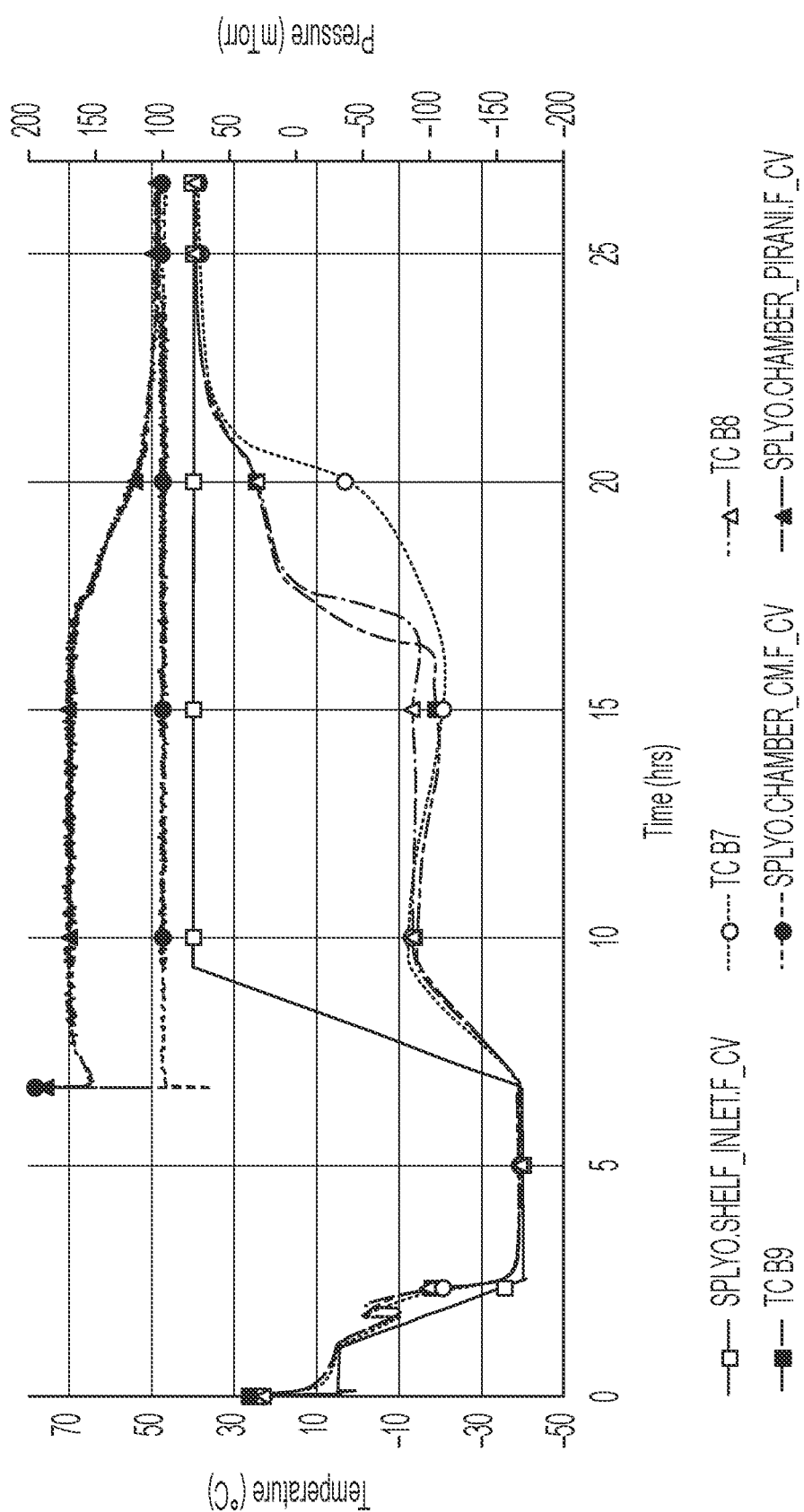

For the second product temperature run (FIG. 6B), the product was loaded at a shelf temperature of 5° C. and held for sixty (60) minutes; then for freezing, the shelf temperature was ramped to −40° C. at 0.5° C./min and held for four (4) hours; and then for sublimation drying followed by additional drying, a vacuum of 100 mTorr was applied and the shelf temperature was ramped to 40° C. at 0.5° C./min and held for seventeen (17) hours. Sublimation drying was competed several hours before the end of the seventeen (17) hour hold at 40° C.

The critical product temperature determined during the sublimation drying for the second product temperature run (FIG. 6B) was to −12.2° C., −14.1° C., and −13.5° C. for formulations B7, B8, and B9 respectively. When the product temperatures were approximately −13° C., all formulations had acceptable cakes and no collapse was seen. The reconstitution time was approximately 1.75 minutes, 4 minutes, and 4 minutes for formulations B7, B8, and B9 respectively.

Figure 6C:
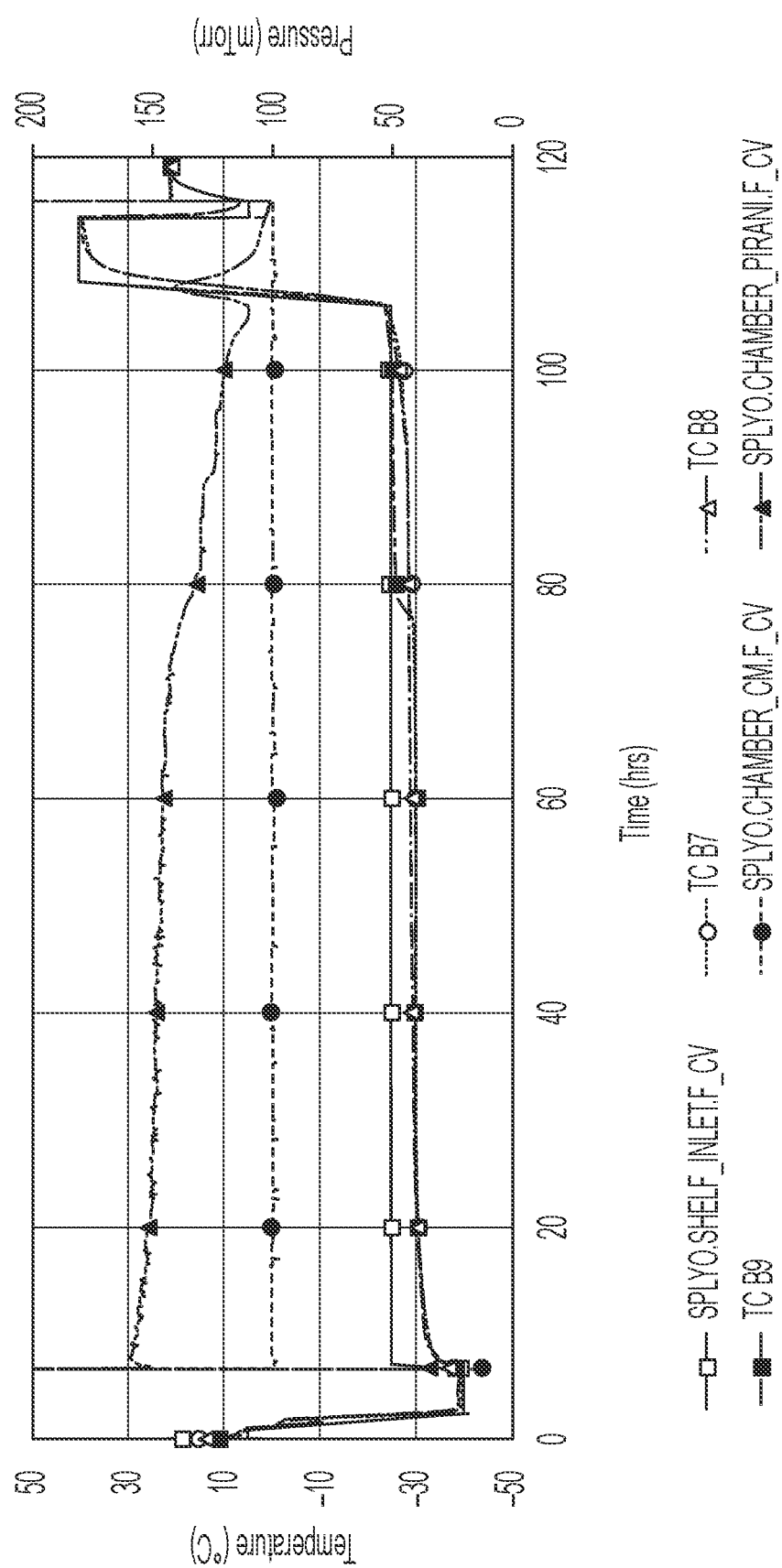

For the third product temperature run (FIG. 6C), the product was loaded at a shelf temperature of 5° C. and held for sixty (60) minutes; then for freezing, the shelf temperature was ramped to −40° C. at 0.5° C./min and held for four (4) hours; then for sublimation drying, a vacuum of 100 mTorr was applied and the shelf temperature was ramped to −25° C. at 0.5° C./min and held until the product temperature of all three formulations reached about −25° C. (about one hundred (100) hours for formulations B7 and B8); and then for additional drying, the shelf temperature was ramped to 40° C. at 0.5° C./min and held for 360 minutes. Formulation B9 reached the shelf temperature of −25° C. in advance of the other samples, and consequently completed sublimation drying earlier than the B7 and B8.

The critical product temperature determined during primary drying for the third critical product temperature run (FIG. 6C) was to −28.5° C., −28.4° C., and −30.0° C. for formulations B7, B8, and B9 respectively. When the product temperatures were approximately −29° C., all formulations had acceptable cakes and no collapse was seen. The reconstitution time was approximately 1.75 minutes, 4 minutes, and 4 minutes for formulations B7, B8, and B9 respectively.

In conclusion, there was no difference in the product appearance based on the critical product temperature during primary drying, even when the critical product temperature during primary drying reached approximately −12° C. No collapse was seen.

Example 2

A study prepared daptomycin/sorbitol/mannitol development stability units and tested the stability of the lyophilized samples over storage and after reconstitution. Test articles consist of the daptomycin formulation with variations of pH and excipient concentrations. The test article formulations are shown in FIG. 7. The formulations were filled into 10 mL vials and freeze-dried. The vials were stored inverted at 25° C., 30° C., and 40° C. Results are shown in FIG. 8.

Example 3

A study investigated the effect of different moisture levels on the stability of lyophilized daptomycin formulations containing a preferred combination of sorbitol and mannitol (Formulation B7: 105 mg/mL daptomycin, 5% sorbitol, 5% mannitol, pH 6.8). Secondary drying temperatures were selected to obtain desired moisture levels for stability.

Specifically, sorbitol and mannitol were dissolved in approximately 250 mL of water in a jacked vessel controlled to 5° C. Daptomycin was dissolved in the solution over the period of 115 minutes (initial pH 4.26 at 6.1° C.). NaOH was added, and the solution was brought to a final volume of 500 mL with water (final pH was 6.81 at 21.9° C.). The solution was filtered, and vials were filled with 5 mL of solution and placed in the center of the tray. The rest of the tray was filled with placebo vials which were reconstituted with 4.63 mL of water and allowed to dissolve. The vials were placed in freeze drier and lyophilized.

Samples were grouped into five residual moisture levels and placed on stability at 25° C. and 30° C. for 12 months. At each timepoint, i.e., initial, one month, two months, three months, six months, and twelve months, the reconstitution, appearance, pH, and HPLC assay were measured or performed. Additional moisture analysis was performed for samples stored for 12 months at 25° C. and 30° C.

For formulation characterization, the moisture levels of vials of daptomycin were analyzed by near-infrared spectroscopy (NIR) for time zero and 1 month testing intervals. The average moisture level results from NIR are shown in the table in FIG. 9.

To determine the effect of moisture on stability, moisture results were measured by Karl Fischer titration (KF) at T0, 1 month and 12 months of storage at 25° C. Daptomycin samples tested at T0 and 1-month storage were compared to the values as determined by NIR (FIG. 10). FIG. 11 shows the 25° C. stability data through 12 months of testing. There were no visual appearance issues in either the lyophilized or reconstituted products. Additionally, the pH and reconstitution time did not change significantly over the course of 12 months at 25° C.

The increase in Impurity D7 is significantly higher at higher residual moisture levels. In conclusion, the residual moisture of the product should be controlled to about 1.0% or below to reduce the formation of D7.

Example 4

A study investigated daptomycin formulations with varying amounts of sorbitol, sucrose, and mannitol, as well as changes in pH. Specifically, test and control articles were stored at 25° C., 30° C., and 40° C.; and then at times 0, 1, 2, 3, and 6 months, the samples were reconstituted using 5 mL of distilled water and tested. In this regard, at each time, the formulations were assayed by UPLC whose conditions are described in FIG. 3. Each test article was a solution containing 105 mg/mL daptomycin. The excipients varied as outlined in the tables in FIGS. 12 and 13; and the pH was adjusted to 6.8, unless noted otherwise in table in FIG. 14.

For testing stability, the control and test articles were stored at 25° C. over 6 months. Formulations N1 through N25 were reconstituted with 5 mL of water and tested for related substances. Impurity D7 was measured for formulation samples N1 through N25 stored at 25° C. over 6 months.

Selected results from one month, two months and three months of storage at 25° C. are shown in the table in FIG. 15. The full set of results from six months of storage at 25° C. are shown in the table in FIG. 16; and selected results from this full table are shown in the table in FIG. 17 (all with respect to Impurity D7). In FIGS. 15 and 17, Formulation N11 is representative of a non-limiting example embodiment of the invention and is identified by an asterisk, and Formulation N21 is representative of a control formulation using sucrose without any sugar alcohol and is identified by a plus sign.

For change in impurity D7 over 6 months at 25° C., the presence of sorbitol was important to control the growth. The sorbitol/mannitol mixtures performed better than either mannitol alone or sorbitol alone. Impurity D7 forms more rapidly at higher pH as seen in Formulation N25, however this amount is still less than formulations containing 100% mannitol/sorbitol and high polyol to drug ratio formulations. The combination of sorbitol and mannitol, which are just isomeric polyols, gives surprisingly better results than either excipient alone.

Another factor affecting stability of the lyophilized formulation was the excipient to drug ratio. If the excipient to drug level was too low, it did not provide adequate stabilization (Formulations N5, N9, N13, N17). If the excipient to drug level was too high, it affected the glass transition temperature Tg (Formulations N12, N16, N20; see FIG. 12) which contributed to degradation of the drug product. The glass transition temperature is not the sole indicator of formulation stability because Formulations N13 and N17 had high Tg's, but total impurity growth at 25° C. after 6 months was near 2%.

In conclusion, Formulations N1-N20 were formulated at 105 mg/mL daptomycin with 1.3, 5.0, 8.5, 13.0 excipient-to-drug molar ratios. Sorbitol concentration levels were 0%, 30%, 50%, 70%, and 100% (relative to total amount of excipient, remainder being mannitol). Samples were stored at 25° C. and tested over 6 months. Each sample was reconstituted with 5 mL of water and tested for impurities. Statistical analysis was performed. Formulations with both mannitol and sorbitol stabilized the daptomycin drug product better with respect to Impurity D7 than either mannitol or sorbitol alone. Another factor affecting stability of the lyophilized formulation was the excipient to drug ratio. If the excipient to drug ratio was too low it didn't provide adequate stabilization. If the excipient to drug ratio was too high, the glass transition temperature Tg was decreased which contributed to degradation of the drug product.

FIG. 18 is a table showing some of the test articles from Example 4 which limited the increase in Impurity D7 after storage at 25° C. for 6 months to an increase no greater than about 1.00% relative to the amount at the beginning of storage (e.g., N6, N8, N10, N11, N14 and N15), and also embodiments reasonably interpolated from these test articles to likewise limit the increase in Impurity D7 after storage at 25° C. for 6 months to an increase no greater than about 1.00%. The table includes component amounts calculated for the dried cake (excluding moisture, which is up to about 1.0 wt. %).

Example 5

A study investigated 18 months of long-term data (25° C. storage) for three batches of daptomycin formulation N11, which is representative of an embodiment provided by the present disclosure, as this formulation had been previously studied in the preceding examples. Specifically, each batch had a formulation of 105 mg/mL daptomycin, 5% mannitol and 5% sorbitol, which was filled into vials and lyophilized (both excipient percentages=g/100 mL of solution, as defined earlier herein). The average values for impurity D7 and total impurities are summarized for each of the three batches in the table in FIG. 19 (both impurity amounts=% w/w, as defined earlier herein).

Surprisingly, the results demonstrate the long-term behavior of daptomycin formulation N11 is at least the same or even better than seen in the short-term studies already discussed above. For example, in FIG. 17, the daptomycin formulation N11 had a 0.27% growth of D7 over 6 months storage at 25° C., when compared to 1.82% growth in the control, relative to the amount at the beginning of storage. As shown in FIG. 19, the change in D7 over the first 6 months in the three batches of Example 5 were 0.21, 0.14 and 0.16% respectively, relative to the amount at the beginning of storage. Over 18 months of storage, the change in D7 is 0.50, 0.45 and 0.44% respectively, relative to the amount at the beginning of storage. This data shows that the daptomycin formulation N11 effectively controls impurity formation in the product over the shelf-life.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method of making a pharmaceutically acceptable solid composition comprising daptomycin, the method comprising drying an aqueous solution to form the solid composition with a moisture content of about 1.0 wt. % or less relative to total weight of the solid composition, the aqueous solution comprising (a) water, (b) the daptomycin, (c) sorbitol in an amount of about 1.2 wt. % to about 9.0 wt. % of total volume of the aqueous solution and (d) mannitol in an amount of about 0.6 wt. % to about 9.5 wt. % of the total volume of the aqueous solution, and the aqueous solution contains less than about 0.5 wt. % buffering agent.

2. The method of claim 1, wherein the sorbitol is about 4.0 wt. % to about 5.0 wt. % of the total volume of the aqueous solution, and the mannitol is about 4.0 wt. % to 5.0 wt. % of the total volume of the aqueous solution.

3. The method of claim 1, wherein the aqueous solution has a daptomycin:(sorbitol+mannitol) molar ratio from about 1:4 to about 1:13 and a sorbitol:mannitol weight ratio from 20:80 to 40:60.

4. The method of claim 1, wherein the aqueous solution has a daptomycin:(sorbitol+mannitol) molar ratio from about 1:5 to about 1:13 and a sorbitol:mannitol weight ratio of about 30:70.

5. The method of claim 1, wherein the aqueous solution has a daptomycin:(sorbitol+mannitol) molar ratio from about 1:4 to about 1:9 and a sorbitol:mannitol weight ratio above 40:60 up to 90:10.

6. The method of claim 1, wherein the aqueous solution has a daptomycin:(sorbitol+mannitol) molar ratio from about 1:4 to about 1:8.5 and a sorbitol:mannitol weight ratio about 50:50 to about 70:30.

7. The method of claim 1, comprising adjusting the pH of the aqueous solution to about 4.5 to about 8.0 before the drying of the aqueous solution.

8. The method of claim 1, comprising adjusting the pH of the aqueous solution to about 7.0 before the drying of the aqueous solution.

9. The method of claim 1, wherein the aqueous solution contains substantially no sugars and/or contains substantially no other polyols additional to the sorbitol and the mannitol.

10. The method of claim 1, wherein the aqueous solution contains less than about 0.1 wt. % buffering agent.

11. The method of claim 1, wherein the aqueous solution consists essentially of the daptomycin, the sorbitol, the mannitol, and the water.

12. The method of claim 1, wherein the pharmaceutically acceptable solid composition has an increase in Impurity D7, after storage at 25° C. for 6 months after the drying of the aqueous solution, that is no greater than about 1.00% relative to an initial amount of the Impurity D7 in the pharmaceutically acceptable solid composition at the beginning of the storage, as measured by peak area of the Impurity D7 divided by peak area of the daptomycin and total impurities using Ultra Performance Liquid Chromatography.

13. The method of claim 1, wherein the drying comprises a sublimation drying at a temperature of about −25° C. to about 50° C. for a time period of about 15 hours to about 120 hours.

14. The method of claim 13, wherein the temperature of the sublimation drying is about 10° C. to about 20° C., and the time period of the sublimation drying is about 18 hours to about 25 hours.

15. The method of claim 13, wherein the drying is a process selected from the group consisting of (i) the process comprises the sublimation drying, (ii) the process comprises the sublimation drying and one or more preceding drying steps, (iii) the process comprises the sublimation drying and one or more subsequent drying steps and (iv) the process comprises the sublimation drying, one or more preceding drying steps, and one or more subsequent drying steps.

16. A pharmaceutically acceptable solid composition made by the method of claim 1.

17. A pharmaceutically acceptable solid composition comprising daptomycin and a combination of sorbitol and mannitol and having a moisture content of about 1.0 wt. % or less, wherein the sorbitol is about 6.2 wt. % to about 45.3 wt. % of total weight of the pharmaceutically acceptable solid composition, the mannitol is about 3.1 wt. % to about 47.5 wt. % of the total weight of the pharmaceutically acceptable solid composition, and the total of the sorbitol and the mannitol is about 31.0 wt. % to about 59.4 wt. % of the total weight of the pharmaceutically acceptable solid composition.

18. The pharmaceutically acceptable solid composition of claim 17, having a daptomycin:(sorbitol+mannitol) molar ratio from about 1:4 to about 1:13 and a sorbitol:mannitol weight ratio from 20:80 to 40:60.

19. The pharmaceutically acceptable solid composition of claim 18, wherein the daptomycin:(sorbitol+mannitol) molar ratio is from about 1:5 to about 1:13, and the sorbitol:mannitol weight ratio is about 30:70.

20. The pharmaceutically acceptable solid composition of claim 18, wherein the sorbitol is about 6.2 wt. % to about 22.1 wt. % of the total weight of the pharmaceutically acceptable solid composition, the mannitol is about 18.6 wt. % to about 47.5 wt. % of the total weight of the pharmaceutically acceptable solid composition, and the total of the sorbitol and the mannitol is about 31.0 wt. % to about 59.4 wt. % of the total weight of the solid composition.

21. The pharmaceutically acceptable solid composition of claim 18, wherein the aqueous solution has a daptomycin:(sorbitol+mannitol) molar ratio from about 1:4 to about 1:9 and a sorbitol:mannitol weight ratio above 40:60 up to 90:10.

22. The pharmaceutically acceptable solid composition of claim 21, wherein the daptomycin:(sorbitol+mannitol) molar ratio is from about 1:4 to about 1:8.5, and the sorbitol:mannitol weight ratio is about 50:50 to about 70:30.

23. The pharmaceutically acceptable solid composition of claim 21, wherein the sorbitol is about 15.5 wt. % to about 45.3 wt. % of the total weight of the pharmaceutically acceptable solid composition, the mannitol is about 3.1 wt. % to about 25.2 wt. % of the total weight of the pharmaceutically acceptable solid composition, and the total of the sorbitol and the mannitol is about 31.0 wt. % to about 50.3 wt. % of the total weight of the pharmaceutically acceptable solid composition.

24. The pharmaceutically acceptable solid composition of claim 17, having an increase in Impurity D7, after storage at 25° C. for 6 months after the drying of the aqueous solution, that is no greater than about 1.00% relative to an initial amount of the Impurity D7 in the pharmaceutically acceptable solid composition at the beginning of the storage, as measured by peak area of the Impurity D7 divided by peak area of the daptomycin and total impurities using Ultra Performance Liquid Chromatography.

25. The pharmaceutically acceptable solid composition of claim 17, which contains substantially no sugars and/or contains substantially no other polyols additional to the sorbitol and the mannitol.

26. The pharmaceutically acceptable solid composition of claim 17, which contains substantially no buffering agent.

27. The pharmaceutically acceptable solid composition of claim 17, which consists essentially of the daptomycin, the sorbitol, the mannitol, and the moisture content of about 1.0 wt. % or less.

28. The pharmaceutically acceptable solid composition of claim 17, further comprising sodium hydroxide and hydrogen chloride.

29. A method of treating a bacterial infection in a subject having the bacterial infection, the method comprising:
preparing a pharmaceutical product, wherein the preparing of the pharmaceutical product comprises reconstituting, in a pharmaceutically acceptable diluent, the pharmaceutically acceptable solid composition of claim 17; and
administering an effective amount of the pharmaceutical product to the subject.

30. The method of claim 29, wherein the administering comprises intravenous administration.

* * * * *